| United States Patent [19] | [11] Patent Number: 4,992,599 |
|---|---|
| Talbiersky et al. | [45] Date of Patent: Feb. 12, 1991 |

[54] NOVEL PURIFICATION PROCESS

[75] Inventors: Jorg Talbiersky, Dorsten; Bernhard Wefringhaus, Castrop-Rauxel; Konrad Stolzenberg, Waltrop; Wolfgang Bergins, Castrop-Rauxel, all of Fed. Rep. of Germany

[73] Assignee: Rutgerswerke AG, Fed. Rep. of Germany

[21] Appl. No.: 450,050

[22] Filed: Dec. 13, 1989

[30] Foreign Application Priority Data

Dec. 19, 1988 [DE] Fed. Rep. of Germany ....... 3842693
Apr. 18, 1989 [DE] Fed. Rep. of Germany ....... 3912670

[51] Int. Cl.$^5$ .................... C07C 37/74; C07C 37/68
[52] U.S. Cl. .................................. 568/759; 568/748; 568/749
[58] Field of Search ................. 568/759, 749, 748

[56] References Cited

PUBLICATIONS

Mark, "Chemical Abstracts" vol. 89 (1978) 89:129251z.
Bridwell, "Chemical Abstracts" vol. 89 (1978) 89:129254c.
Hoeringklee, "Chemical Abstracts" vol. 102 (1985) 102:45616w.

Primary Examiner—Werren B. Lone
Attorney, Agent, or Firm—Bierman and Muserlian

[57] ABSTRACT

Crude phenol and also individual phenol fractions from tars or the hydrogenation of coal are purified from contaminating organic bases and sulfur compounds by treating the phenols with phthalic acid anhydride and optionally a quinone and distillation.

8 Claims, No Drawings

NOVEL PURIFICATION PROCESS

STATE OF THE ART

Crude phenols and phenol fractions from tars or hydrogenation of coal contain organic bases and sulfur compounds which are very difficult to separate from the phenols and then only by individual process steps as indicated in Dienchs/Kubicka Phenole and Basen, Akademie-Verlag, Berlin, 1958, pp 344 ff.

OBJECTS OF THE INVENTION

It is an object of the invention to provide a simple and economical process for the simultaneous removal of nitrogen and sulfur containing impurities from phenolic compositions.

This and other objects and advantages of the invention will become obvious from the following detailed description.

IN THE INVENTION

The novel process of the invention for simultaneously removing organic bases and sulfur compounds from phenolic fractions comprises reacting the phenolic fractions at elevated temperatures with phthalic acid anhydride and distilling the mixture to obtain a purified phenol.

It has been found that by thermal treatment of phenols with 1 to 5% by weight of phthalic acid anhydride (PAA) and subsequent fractional distillation, the content of both bases and sulfur of the phenols is reduced. At the same time, the color stability is increased as well. A further improvement of the purification action and also improvement of the color stability is achieved if in the thermal treatment with phthalic acid anhydride, small amounts i.e. 0.01 to 0.5% by weight, based on the quantity of phenols, of a quinone are added. This is especially surprising inasmuch as by treatment with quinone along, no effect is obtained.

Examples of quinones are all para-or amphi-quinones such as e.g. benzoquinone, napththoquinone, anthraquinone or the respective alkyl-substituted quinones. The best results are obtained with the use of anthraquinone. Here it was found that as thermal treatment the heat treatment occurring in a distillation under mild conditions is sufficient if crude phenols are used which have a high disulfide content and a relatively low content of mercapto groups.

The process of the invention comprises by mixing the crude phenol or the phenol fraction to be treated with the phthalic acid anhydride or with the phthalic acid anhydride and quinone and heating with stirring for several hours i.e., 5 to 30 hours at a temperature in the range of 100° to 180° C. Then, the reaction mixture is fractionally distilled and the undesired impurities remain in the distillation residue.

In an improved embodiment, the phenols are admixed with 1 to 5% by weight of phthalic acid anhydride or respectively with 1 to 5% by weight phtalic acid anhydride and 0.01 to 0.5% by weight of a quinone, based on the amount of phenol and optionally an aromatic hydrocarbon and are heated for 5 to 30 hours at reflux. This is followed by fractional distillation, preferably under vacuum. Preferred aromatic hydrocarbons are those boiling in the range of 100° to 150° C., such as e.g. toluene, ethylbenzene or xylenes.

In the preferred embodiment, the phenols whose content of disulfide groups had been increased by previous oxidative treatment, are admixed with 1 to 5% by weight of phthalic acid anhydride and 0.01 to 0.5% by weight of anthraquinone and are distilled at as low as possible a sump temperature and with a short dwell time. Such a distillation under mild conditions is e.g. a distillation under vacuum, i.e. 30–80 mbars, preferably in short-path distilling apparatus such as thin-layer or falling film vaporizers.

A further simplification in the handling of the high melting point substances of phthalic acid anhydride and quinone consists in dissolving these reactants in high-boiling phenols and they can be charged in solution form which is easy to proportion, and there remains a distillation residue easy to handle.

In the following examples there are described several preferred embodiments to illustrate the invention. However, it is to be understood that the invention is not intended to be limited to the specific examples.

EXAMPLE 1

4,000 g of crude phenol of the following composition

| | |
|---|---|
| phenol | 61.6% |
| o-cresol | 10.35% |
| m/p cresol | 20.15% |
| 2,6 dimethyl phenol | 0.55% |
| o-ethyl phenol | 0.20% |
| 2,4/2,5-dimethyl phenol | 3.10% |
| 3,5-dimethyl phenol + m/p-ethyl phenol | 2.45% |
| 2,3 dimethyl phenol | 0.30% |
| 3,4-dimethyl phenol | 0.30% |
| p-isopropyl phenol | 0.90% |
| $C_9$-phenols | 0.10% | were admixed with a solution of 100 g of phthalic acid anhydride (PAA), or respectively 100 g of phthalic acid anhydride and 0.8 g of anthraquinone in high-boiling phenols as well as with 200 ml of xylene (isomeric mixture) and the mixture was refluxed for 24 hours. Then, the reaction mixture was fractionally distilled at 133 mbars. The following Table 1 shows the results obtained in comparison with a crude phenol sample subjected to the same procedure, but to which neither phthalic acid anhydride nor anthraquinone had been added (control). The respective values for the individual phenol fractions are found in Tables 2 and 3. Table 4 shows the color stabilities of the individual fractions measured after 24 days by the method of ASTM 1986-61.

TABLE 1

Combined removal of organic base and sulfur impurities of crude phenol (total distillate)

| Agent: | PAA | PAA + anthraquinone | Control |
|---|---|---|---|
| Distillation yield | 95% | 92% | 93% |
| Base reduction in total distillate referred to base content in charge | 82% | 86% | 60% |
| Base content in total distillate | 298 ppm | 240 ppm | 683 ppm |
| Sulfur reduction in total distillate referred to sulfur content in charge | 52% | 82% | 31% |
| Sulfur content in total distillate | 112 ppm | 43 ppm | 163 ppm |

TABLE 2

| Debasing of crude phenol Agent: | PAA | PAA + anthraquinone | Control |
|---|---|---|---|
| Base content (ppm) in: | | | |

TABLE 2-continued

| Debasing of crude phenol Agent: | PAA | PAA + anthraquinone | Control |
|---|---|---|---|
| Phenol first running | 3 (−99)[1] | 6 (−97.9)[1] | 284 |
| Phenol | 6 — | 2 — | 6 |
| o-Cresol | 170 (−92.4) | 129 (−94.3) | 2251 |
| m/p Cresol | 559 (−64.5) | 640 (−59.3) | 1574 |

[1]In parentheses: Deviation of the base content from the control in %.

TABLE 3

| Desulfuring of of crude phenol Agent: | PAA | PAA + anthraquinone | Control |
|---|---|---|---|
| Sulfur content (ppm) in: | | | |
| Phenol first running | 296 (−82.6)[1] | 327 (−80.8)[1] | 1708 |
| Phenol | 17 (−37) | 16 (−40.7) | 27 |
| o-Cresol | 16 (−63.6) | 11 (−75.0) | 44 |
| m/p-Cresol | 31 (−44.8) | 17 (−74.6) | 67 |

[1]In parentheses: Deviation of the sulfur content from the control in %.

TABLE 4

| Color stability of the crude phenol fractions | | | |
|---|---|---|---|
| Agent: | PAA | PAA + anthraquinon | Control |
| Color of the fraction after 24 days (Apha) | | | |
| Phenol first running | 100 | 20 | >250 |
| Phenol | 85 | 25 | >250 |
| o-Cresol | 10 | 20 | 100 |
| m/p-Cresol | 7 | 25 | >250 |

EXAMPLE 2

| Test A: Crude phenol charged (high conversion to disulfide) | |
|---|---|
| Total sulfur content: | 165 ppm |
| Mercapto sulfur: | 5 ppm |
| Bases | 1616 ppm |
| Test B: Crude phenol charged (low conversion to disulfide) | |
| Total sulfur: | 240 ppm |
| Mercapto sulfur | 184 ppm |

-continued

| EXAMPLE 2 | |
|---|---|
| Bases: | 1010 ppm |

In both crude phenols, 2.5% by weight of phthalic acid anhydride and 0.2% by weight of anthraquinone were dissolved, and these solutions were distilled without further thermal pretreatment within 45 minutes at 66 mbars. The distillation reduction was 90%. The results obtained are listed in Table 5.

TABLE 5

| Crude phenol type | Temperature Head °C. | Temperature Sump °C. | Bases in distillate ppm | Degree of debasing % | Sulfur in distillate ppm | Degree of desulfuring. % |
|---|---|---|---|---|---|---|
| A | 106–117 | 114–130 | 246 | 86.3 | 4 | 97.8 |
| B | 106–117 | 114–130 | 154 | 86.2 | 176 | 34.0 |

Various modifications of the process of the invention may be made without departing from the spirit and scope thereof and it is to be understood that the invention is intended to be limited only as defined in the appended claims.

What we claim is:

1. A process for simultaneously removing organic bases and sulfur compounds from phenolic fractions from tars or hydrogenation of coal comprising reacting the phenolic fraction at temperatures of about 100° to 180° with phthalic acid anhydride and distilling the mixture to obtain a purified phenol.

2. The process of claim 1 wherein a quinone is added with the phthalic acid anhydride.

3. The process of claim 2 wherein the amount of quinone is 0.01 to 0.5% by weight.

4. The process of claim 2 wherein the quinone is another quinone.

5. The process of claim 4 wherein the reaction at elevated temperature occurs with a distillation under mild conditions.

6. The process of claim 1 wherein the phthalic acid anhydride is added as to solution in a high-boiling phenol.

7. The process of claim 2 wherein the phthalic acid anhydride and quinone are added as a solution in a high-boiling phenol.

8. A process for simultaneously removing organic bases and sulfur containing compounds from phenolic containing compositions comprising refluxing a mixture of the phenolic containing composition, an aromatic hydrocarbon and 1 to 5% by weight of phthalic acid anhydride for 5 to 30 hours and subjecting the mixture to vacuum distillation.

* * * * *